(12) United States Patent
Zhang et al.

(10) Patent No.: US 10,699,887 B2
(45) Date of Patent: Jun. 30, 2020

(54) PREPARATION AND FEED APPARATUS OF STANDARD SAMPLE FOR CALIBRATION OF TRACE-ANALYSIS INSTRUMENT

(71) Applicant: NUCTECH COMPANY LIMITED, Beijing (CN)

(72) Inventors: Qingjun Zhang, Beijing (CN); Yuanjing Li, Beijing (CN); Ziran Zhao, Beijing (CN); Weiping Zhu, Beijing (CN); Nan Bai, Beijing (CN); Qiufeng Ma, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 443 days.

(21) Appl. No.: 15/786,389

(22) Filed: Oct. 17, 2017

(65) Prior Publication Data

US 2018/0158659 A1 Jun. 7, 2018

(30) Foreign Application Priority Data

Dec. 7, 2016 (CN) .......................... 2016 1 1116486

(51) Int. Cl.
*H01J 49/00* (2006.01)
*G01N 33/00* (2006.01)
(Continued)

(52) U.S. Cl.
CPC ........ *H01J 49/0009* (2013.01); *B01L 3/5025* (2013.01); *B01L 3/523* (2013.01);
(Continued)

(58) Field of Classification Search
CPC .. B01L 2200/12; B01L 2300/06; B01L 3/523; B01L 3/5025; G01N 1/38; G01N 1/10; G01N 1/28; G01N 33/558; G01N 2001/386; G01N 35/10; G01N 35/1002; G01N 35/1095; G01N 2001/2893;
(Continued)

(56) References Cited

U.S. PATENT DOCUMENTS 3,160,486 A * 12/1964 Busch, Jr. ............... F15B 11/15
137/624.14
3,401,565 A * 9/1968 Stoll ...................... G01N 30/12
73/863.11

(Continued)

*Primary Examiner* — Daniel S Larkin
*Assistant Examiner* — Anthony W Megna Fuentes
(74) *Attorney, Agent, or Firm* — BakerHostetler

(57) ABSTRACT

Embodiments of the present disclosure relate to a preparation and feed apparatus of a standard sample for calibration of a trace-analysis instrument, and especially to a preparation and feed apparatus of a standard sample for calibration of a gas chromatograph-ion mobility spectrometer. When the trace-analysis instrument is being calibrated by taking advantage of the preparation and feed apparatus according to embodiments of the disclosure, it is unnecessary to use an additional dedicated tool and steps to prepare the sample for testing and to use an organic solvent or a dedicated sample application/dispensing tool, resulting in that the trace-analysis instrument is simple and convenient to carry and use, and the substance for calibration is also convenient to store and exchange; moreover, the trace-analysis instrument is also safe, reliable and environmentally friendly.

19 Claims, 4 Drawing Sheets

(51) Int. Cl.
*G01N 15/10* (2006.01)
*G01N 35/10* (2006.01)
*G01N 1/38* (2006.01)
*G01N 1/28* (2006.01)
*G01N 33/558* (2006.01)
*G01N 30/06* (2006.01)
*G01N 30/12* (2006.01)
*G01N 30/16* (2006.01)
*B01L 3/00* (2006.01)
*G01N 1/10* (2006.01)
*G01N 1/40* (2006.01)
*H01J 49/04* (2006.01)
G01N 30/00 (2006.01)
G01N 30/18 (2006.01)
G01N 30/04 (2006.01)
G01N 1/00 (2006.01)

(52) U.S. Cl.
CPC ............. *G01N 1/10* (2013.01); *G01N 1/28* (2013.01); *G01N 1/38* (2013.01); *G01N 1/405* (2013.01); *G01N 15/1012* (2013.01); *G01N 30/06* (2013.01); *G01N 30/12* (2013.01); *G01N 30/16* (2013.01); *G01N 33/0006* (2013.01); *G01N 33/0013* (2013.01); *G01N 33/0031* (2013.01); *G01N 33/558* (2013.01); *G01N 35/10* (2013.01); *G01N 35/1002* (2013.01); *G01N 35/1095* (2013.01); *H01J 49/0431* (2013.01); *B01L 2200/12* (2013.01); *B01L 2300/06* (2013.01); *G01N 2001/2893* (2013.01); *G01N 2001/386* (2013.01); *G01N 2030/009* (2013.01); *G01N 2030/062* (2013.01)

(58) Field of Classification Search
CPC ........... G01N 33/0006; G01N 15/1012; G01N 30/16; G01N 30/06; G01N 30/12; G01N 1/405; G01N 33/0013; G01N 33/0031; G01N 2030/009; G01N 2030/062; G01N 30/18; G01N 2030/042; G01N 2001/002; H01J 49/0009; H01J 49/0431
See application file for complete search history.

(56) References Cited

U.S. PATENT DOCUMENTS

| 4,124,358 | A | * | 11/1978 | Muller | G01N 30/12 |
|---|---|---|---|---|---|
| | | | | | 73/23.42 |
| 4,128,008 | A | * | 12/1978 | Linenberg | G01N 1/405 |
| | | | | | 73/863.12 |
| 4,732,046 | A | * | 3/1988 | Lawrence | G01N 1/4022 |
| | | | | | 250/282 |
| 5,147,612 | A | * | 9/1992 | Raal | B01F 3/022 |
| | | | | | 137/88 |
| 2004/0235025 | A1 | * | 11/2004 | Mori | B01L 3/0275 |
| | | | | | 435/6.13 |
| 2014/0030818 | A1 | * | 1/2014 | Schueler | G01N 1/2214 |
| | | | | | 436/178 |

* cited by examiner

PREPARATION AND FEED APPARATUS OF STANDARD SAMPLE FOR CALIBRATION OF TRACE-ANALYSIS INSTRUMENT

CROSS-REFERENCE TO RELATED INVENTION

The present disclosure claims the benefit of Chinese Patent Application Invention No. 201611116486.0 filed on Dec. 7, 2016 in the State Intellectual Property Office of China, the whole disclosure of which is incorporated herein by reference.

BACKGROUND OF THE INVENTION

Field of the Invention

Embodiments of the present disclosure pertain to the technical field of on-site detection/inspection of chemical substances, and specifically relate to a calibration of a metrical instrument, and more specifically, to a preparation and feed apparatus of standard sample for calibration of trace-analysis instrument (especially a gas chromatograph-ion mobility spectrometer).

Description of the Related Art

The ion mobility spectrometry (IMS) technology is a technology which implements a rapid trace inspection on chemical substances at atmosphere pressure, and has an extremely high sensitivity and response speed. Ion mobility spectrometry (IMS) technology, due to its characteristics of simple structure, high sensitivity, and rapid analysis, is widely used for detections and monitors in chemical warfare agents, drugs, explosives and other aspects of environmental monitoring. However, as compared with other existing detection technologies, IMS also has several intrinsic restrictions, as below:

Firstly, it is unable to process a chemical mixture sufficiently, since IMS is too ambiguous to be identified or even an ionic spectrum which is indistinguishable may be created, when there is little difference in ion mobility (i.e., migration ratio) among ions in a complex mixture from the ion source. Therefore, when there is a disrupting chemical which contains a plurality of components, IMS tends to bring about an erroneous detection.

Secondly, it has a low linear response range, and thus tends to be saturated, therefore it is necessary to check carefully specific amount of the sample to be detected so as to avoid occurrence of saturation and/or non-linear response.

These intrinsic restrictions of IMS prevent it from functioning as a more favorable analysis tool.

Therefore, one method for overcoming IMS's restrictions is for example to combine it with the GC (i.e., gas chromatograph) technology, so as to form a GC-IMS (gas chromatograph-ion mobility spectrometer). The GC is used as a front-end primary separator of the IMS, and GC provides an advantage of separating the complex mixture into several single components for detection/inspection. Gas chromatography-ion mobility spectrometry (GC-IMS) associated technology with full use of the prominent separation characteristics of the GC and rapid response, high sensitivity and high resolution of the IMS, not only effectively solves both low discriminative ability of the GC and cross sensitivity problem of the IMS during detection of the mixture, but also can obtain the chromatographic retention time, drift time of an ion of an object to be detected in a migration passage and signal strength of the object to be detected finally inducted in the Faraday disc, so that obtained 3D map information of the object to be detected can be used to perform effectively an accurate recognition of the sample with complex components.

Therefore, though GC is not easily influenced by external work environment, its calibration takes time and effort, and it is also meaningless to detect the components of sample which are not to be detected, therefore, it is not necessary to perform calibration separately on GC. However, IMS may be easily influenced by some factors e.g., environmental pressure, and the calibration on IMS is favorable for detection precision of GC-IMS. Therefore, in practice, when GC and IMS are combined to use, e.g, in the form of GC-IMS, then a calibration thereof may be carried out depending on operational environment, so as to ensure reliability of results of the instrumental analysis thereof. Only in the case that migration/mobility times of other detectable materials are adjusted correspondingly depending on practically measured ion migration time of the material component to be calibrated in the sample and its changing situation, it is possible to ensure accuracy of recognition or identification of GC-IMS.

However, a preparation and feed apparatus of a standard sample and method for the same during a conventional IMS calibration fail to be adapted to a GC-IMS (i.e., gas chromatograph-ion mobility spectrometer), and there is no such preparation and feed apparatus of a standard sample and method for the same dedicated to relevant calibration of GC-IMS being mentioned or reported in the prior art.

Therefore, it is necessary to provide a preparation and feed apparatus of a standard sample for calibration of a trace-analysis instrument, especially for a GC-IMS.

SUMMARY OF THE INVENTION

The embodiments of the present disclosure have been made to overcome or alleviate at least one aspect of the above mentioned disadvantages and/or shortcomings in the prior art, in consideration of aforementioned technical problems in the background.

Correspondingly, a technical purpose of the embodiments of the disclosure is to provide a preparation and feed apparatus of a standard sample for calibration of a trace-analysis instrument, which takes advantage of an exchangeable sample vessel so as to facilitate an efficient and clean filling and exchange of the sample, and to carry and operate conveniently, without any additional sample preparation tool or steps; furthermore, the preparation and feed apparatus is also characterized by its safety and environmental protection.

And another purpose of the embodiments of the disclosure is to provide a gas chromatograph-ion mobility spectrometer which uses the preparation and feed apparatus.

Following technical solutions are adopted in exemplary embodiments of the invention for achieving the above desired technical purposes.

According to an aspect of the exemplary embodiment of the present disclosure, there is provided a preparation and feed apparatus of a standard sample for calibration of a trace-analysis instrument, wherein the preparation and feed apparatus comprises: a piston assembly, comprising: a piston cylinder, a piston rod which is received within the piston cylinder and is provided with a storage chamber penetrating radially therethrough, and a diffusion chamber defined inside the piston cylinder and between an inner wall of the piston cylinder and the piston rod; and a steam channel which is arranged outside the piston assembly and is provided with a steam inlet port and a steam outlet port both being in communication with the piston cylinder. The piston rod is configured to be displaceable longitudinally within the piston cylinder, such that the storage chamber is communicable with the steam channel via the steam inlet port, and a condition of communication from the steam outlet port to the diffusion chamber within the piston cylinder is changeable continuously between a completely unobstructed condition and a completely occluded condition via the piston rod.

In an embodiment of the disclosure, the piston assembly further comprises a peripheral sealing ring mounted onto the piston rod, and the peripheral sealing ring is configured to abut in an airtight manner against both the inner wall of the piston cylinder and the piston rod so as to be disposed therebetween, and also configured to be displaceable longitudinally inside the piston cylinder with a displacement of the piston rod.

In an embodiment of the disclosure, the peripheral sealing ring comprises an upper sealing ring and a lower sealing ring which are respectively configured to be disposed at both upper and lower sides of the storage chamber, longitudinally within the piston cylinder.

In an embodiment of the disclosure, the diffusion chamber is delimited between the inner wall of the piston cylinder and the piston rod by the lower sealing ring, and is provided with a volume which is continuously variable with the displacement of the piston rod.

In an embodiment of the disclosure, the preparation and feed apparatus further comprises a clean air channel which is provided outside the piston assembly and in communication with the piston cylinder and an external environment, and is provided with a first-level air-tight valve which is opened unidirectionally towards the piston cylinder.

In an embodiment of the disclosure, the clean air channel comprises a gas filter device provided upstream of the first-level airtight valve.

In an embodiment of the disclosure, the gas filter device comprises a filter cartridge which is filled with activated carbon and molecular sieve.

In an embodiment of the disclosure, the preparation and feed apparatus further comprises a hollow feed syringe needle which is removably mounted at a bottom portion of the piston cylinder and comprises: a needle inlet end which is in fluid communication with the bottom portion of the piston cylinder; and a needle outlet end which extends outwards from the piston cylinder.

In an embodiment of the disclosure, the feed syringe needle is threadedly connected with the bottom portion of the piston cylinder.

In an embodiment of the disclosure, the feed syringe needle is in communication with the bottom portion of the piston cylinder via a second-level airtight valve which is opened unidirectionally from the piston cylinder towards the needle inlet end of the feed syringe needle.

In an embodiment of the disclosure, the airtight valve which is opened unidirectionally is constructed to be of a valve core construction, comprising: a hollow valve core body, comprising a trailing connection portion at a trailing portion of the valve core body, a pagoda-shaped connection head provided at a leading portion of the valve core body, and a valve core middle portion provided between the trailing connection portion and the pagoda-shaped connection head; and an elastic sealing sleeve within which the pagoda-shaped connection head is encapsulated circumferentially. The pagoda-shaped connection head is provided with a valve core exhaust port, which is located laterally at a front end of the pagoda-shaped connection head.

In an embodiment of the disclosure, the storage chamber is configured to accommodate a sample vessel which is removably mounted herein.

In an embodiment of the disclosure, the sample vessel comprises: a hollow housing, which comprises a through-hole in an axial direction thereof and a pair of stepped counter bores recessed axially at both ends thereof, each stepped counter bore comprising a first counter bore and a second counter bore which are arranged co-axially, and the first counter bore having a smaller cross section dimension and a larger depth recessed inwards axially as compared with those of the second counter bore; at least one sample storage device, each of which is provided within the first counter bore and comprises a sample receptacle which is hollow and arranged axially, and a pair of micro-pore filtration membranes which abut axially against both ends of the sample receptacle; and a vessel cover, configured to press one of the pair of micro-pore filtration membrane which is located outside axially, against the sample receptacle.

In an embodiment of the disclosure, the vessel cover is provided with a recess at an inner end thereof, which inner end is arranged to face the sample storage device, the recess being further provided with tooth-shaped projections at an inner surface thereof facing the micro-pore filtration membrane.

In an embodiment of the disclosure, the preparation and feed apparatus further comprises a blowing device provided within or adjacent to the storage chamber in the piston rod.

In an embodiment of the disclosure, the blowing device is located opposite to a side of the storage chamber at which side the storage chamber is in communication with the steam channel, and is in communication with the storage chamber so as to blow inwards the sample vessel.

In an embodiment of the disclosure, the preparation and feed apparatus further comprises a heater provided within or adjacent to the storage chamber in the piston rod.

And according to another aspect of the exemplary embodiment of the present disclosure, there is also provided a gas chromatograph-ion mobility spectrometer, comprising the preparation and feed apparatus as above.

The following description may relate to individual features and combinations thereof. It should be known that both aforementioned general description and following detailed description are only exemplary and explanatory ones, rather than limitations on generalized inventive concept on which the embodiments disclosed by the disclosure are based.

BRIEF DESCRIPTION OF THE DRAWINGS

The above and other features and advantages of the present disclosure will become more apparent and a more comprehensive understanding of the present disclosure can be obtained, by describing in detail exemplary embodiments thereof with reference to the accompanying drawings, in which.

Identical reference numerals are applied to refer to same or corresponding components or features, throughout the drawings.

DETAILED DESCRIPTION OF EMBODIMENTS OF THE INVENTION

Figure 1:
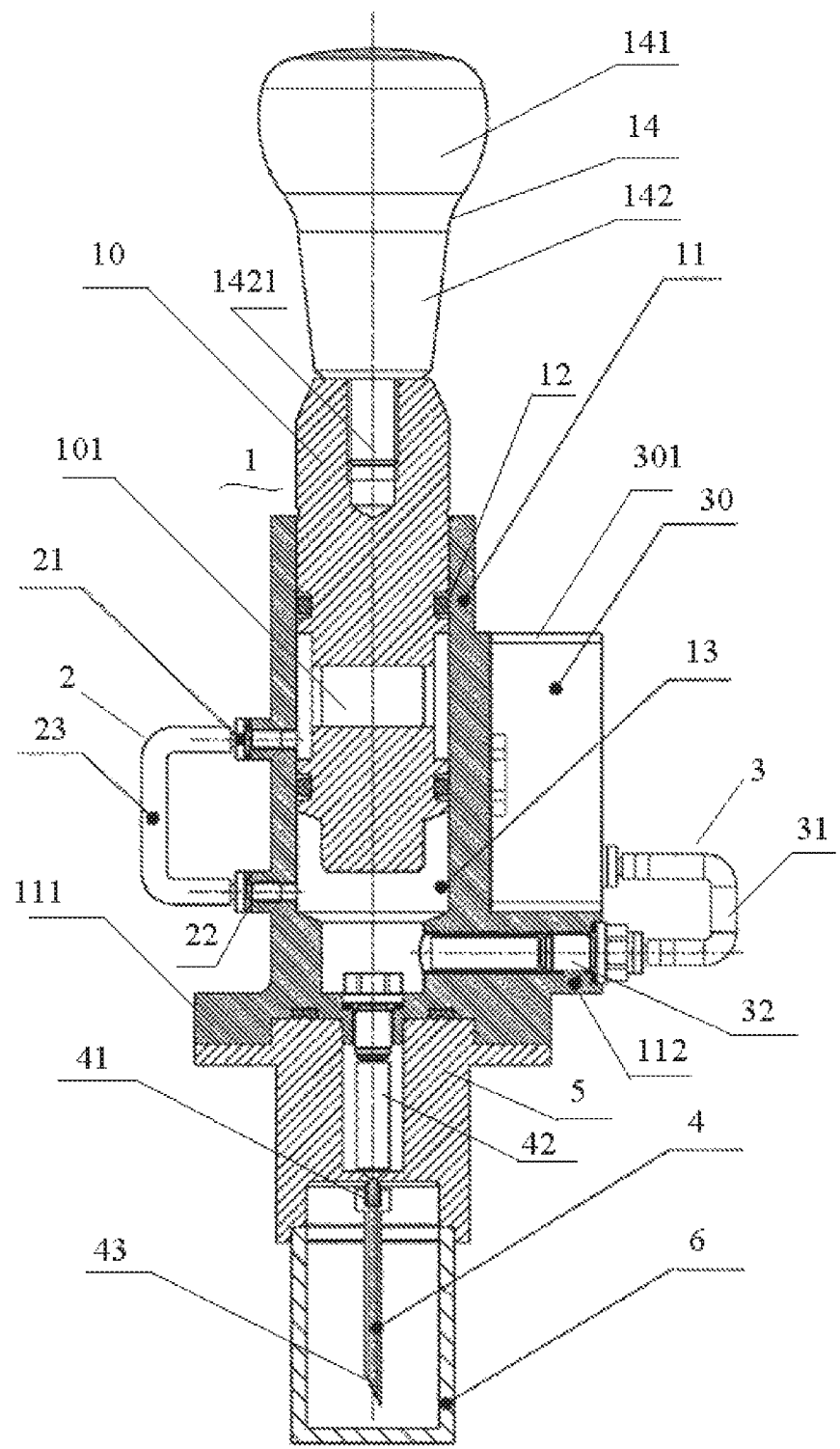
FIG. 1 illustrates a schematic sectional view of a preparation and feed apparatus of a standard sample, in a longitudinal direction thereof, according to a first embodiment of the disclosure, wherein the preparation and feed apparatus is in a process of diffusion of the sample.

Exemplary embodiments of the present disclosure will be described hereinafter in detail with reference to the attached drawings, wherein the like reference numerals refer to the like elements. The present disclosure may, however, be embodied in many different forms, and thus the detailed description of the embodiment of the disclosure in view of attached drawings should not be construed as being limited to the embodiment set forth herein; rather, these embodiments are provided so that the present disclosure will be thorough and complete, and will fully convey the general concept of the disclosure to those skilled in the art.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Respective dimension and shape of each component in the drawings are only intended to exemplarily illustrate the contents of the disclosure, rather than to demonstrate the practical dimension or proportion of elements, components and devices of embodiments of the disclosure.

According to a general technically inventive concept of the present disclosure, as illustrated in FIG. 1, there is provided a preparation and feed apparatus of a standard sample for calibration of a trace-analysis instrument, wherein the preparation and feed apparatus comprises: a piston assembly, comprising a piston cylinder, a piston rod which is received within the piston cylinder and is provided with a storage chamber penetrating radially therethrough; and a diffusion chamber defined inside the piston cylinder and between an inner wall of the piston cylinder and the piston rod; and a steam channel which is arranged outside the piston assembly and is provided with a steam inlet port and a steam outlet port both being in communication with the piston cylinder. The piston rod is configured to be displaceable longitudinally within the piston cylinder, such that the storage chamber is communicable with the steam channel via the steam inlet port, and a condition of communication from the steam outlet port to the diffusion chamber within the piston cylinder may change continuously between a completely unobstructed condition and a completely occluded condition via the piston rod.

Fundamental Embodiment

FIG. 1 illustrates a schematic sectional view of a preparation and feed apparatus of a standard sample, in a longitudinal direction thereof, according to a first embodiment of the disclosure, wherein the preparation and feed apparatus is in a process of diffusion of the sample.

According to an exemplary embodiment of the present disclosure, as illustrated in FIG. 1, there is provided a preparation and feed apparatus of a standard sample for calibration of a trace-analysis instrument, comprising:

a piston assembly 1, comprising a piston cylinder 11, and a piston rod 10 which is movably received within the piston cylinder 11, in a longitudinal direction, and is provided with a storage chamber 101 penetrating radially through the piston rod 11, at a lower end of the piston rod 11; a peripheral sealing ring 12 which is mounted onto the piston rod 10, abut in an airtight manner against both the inner wall of the piston cylinder 11 and the piston rod 10 so as to be disposed therebetween, and configured to be displaceable longitudinally inside the piston cylinder 11 with a displacement of the piston rod 10;

a steam channel 2 for delivery of a steam of the sample, which is arranged outside the piston assembly 1 and is provided with a steam inlet port and a steam outlet port both being in communication with the piston cylinder 11;

a clean air channel 3 for delivery of a clean air, which is provided outside the piston assembly 1 and in communication with both the piston cylinder 11 and an external environment, and is provided with a first-level air-tight valve 32 which is opened unidirectionally inwards the piston cylinder 11; and a hollow feed syringe needle 4 which is mounted at a bottom portion of the piston cylinder 11 and extends longitudinally, and comprises a needle inlet end 41 which is in fluid communication with the piston cylinder 11; and a needle outlet end 43 which extends outwards from the piston cylinder 11, the feed syringe needle 4 being in communication with the bottom portion of the piston cylinder 11 via a second-level air-tight valve 42 which is opened unidirectionally from the piston cylinder 11 towards the needle inlet end 41.

And according to an exemplary embodiment of the disclosure, as illustrated in FIG. 1, the peripheral sealing ring 12 comprises an upper sealing ring 121 and a lower sealing ring 122 both of which are respectively configured to be disposed at both upper and lower sides of the storage chamber 101, longitudinally within the piston cylinder 11; and the piston rod 10, the inner wall of the piston cylinder 11, and the lower sealing ring 122 defines collectively a diffusion chamber 13 thereamong which has a variable volume. As such, on the one hand, the piston cylinder 11 is used to define a scope of the piston rod 10 displaceable therein; on the other hand, the piston cylinder 11 cooperates with both the piston rod 10 and the lower sealing ring 122 so as to define collectively the diffusion chamber which is variable in its volume, for storage of the clean air which is filtered and the steam of the standard sample which diffuses out of the storage chamber 101.

Furthermore, the steam channel 2 is further configured to be in communication with both the storage chamber 101 and the diffusion chamber 13 within the piston cylinder 11, i.e., communicating therebetween, and the clean air channel 3 is further configured to communicate ambient air to the diffusion chamber 13 within the piston cylinder 11.

Figure 5:
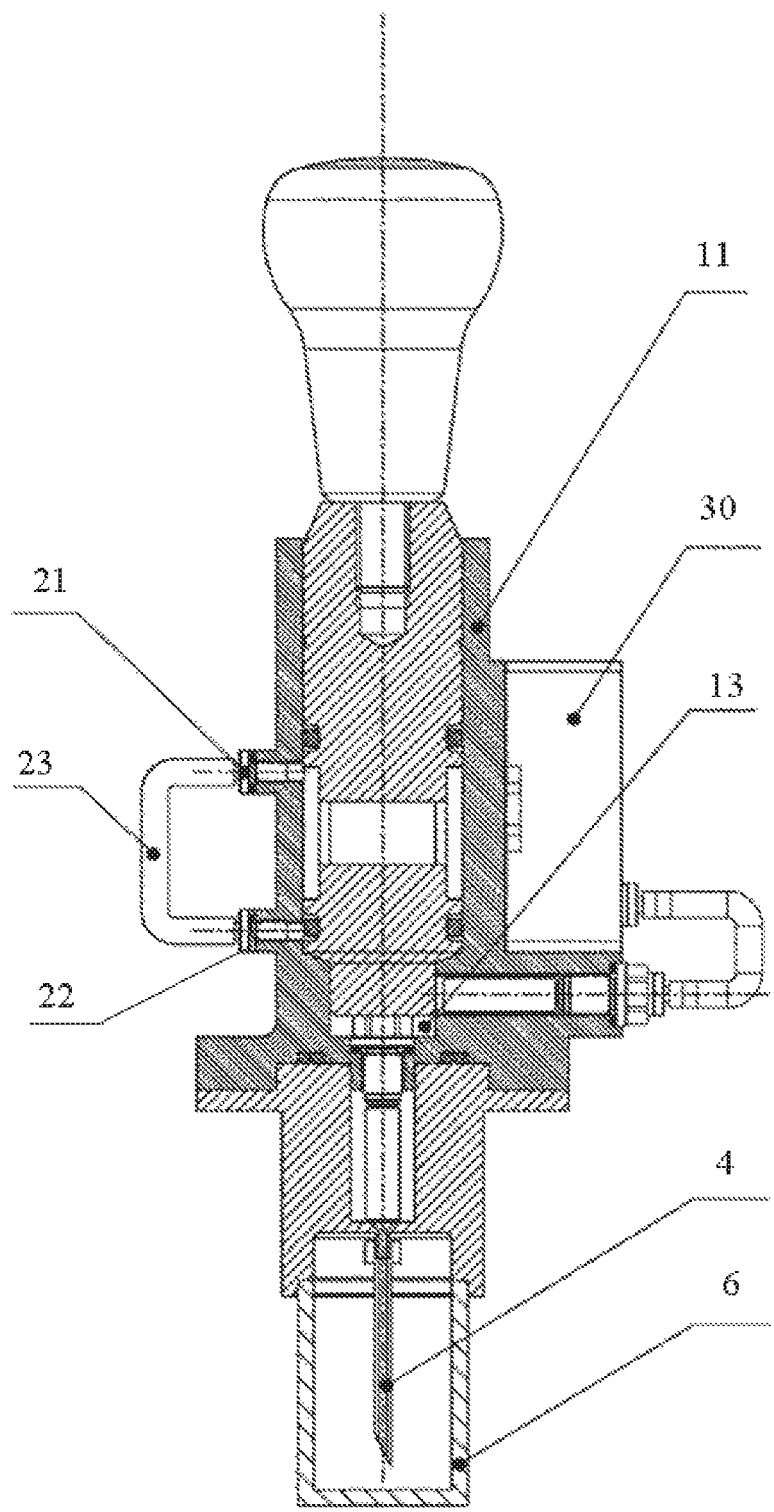
FIG. 5 illustrates a schematic sectional view of the preparation and feed apparatus as illustrated in FIG. 1, in another operation condition thereof, wherein the preparation and feed apparatus is in a process of calibration of the sample introduced therein.

At an initial moment, the piston rod 10 is in a completely compressed condition within the piston cylinder 11; in other words, e.g., as illustrated in FIG. 5, a condition in which the piston rod 10 is compressed to a lowest position within the piston cylinder 11. At that moment, the volume of the diffusion chamber 13 has a minimized value which is substantially equal to zero; and due to existences of both the first-level air-tight valve 32 and the second-level air-tight valve 42 each of which is opened unidirectionally, a fluid path from the external environment via the clean air channel 3 to the diffusion chamber 13 is considered to be in the "unobstructed/opened" condition, and meanwhile another fluid path from the diffusion chamber 13 via the feed syringe needle 4 to the external environment is considered to be in the "occluded/closed" condition, such that an internal pressure of the diffusion chamber 13 may be considered to be essentially equal to an ambient atmosphere pressure. Then, at that time, as illustrated in FIG. 5, the piston rod 10 blocks the communication from the steam outlet port of the steam channel 2 to the piston cylinder 11, such that there is no steam of the sample entering the diffusion chamber 13.

Once starting from the condition of the minimized volume of the diffusion chamber at the initial moment, the piston rod 10 continues to be driven to an highest position inside the piston cylinder 11 so as to maximize the volume of the diffusion chamber 13, e.g., as illustrated in FIG. 1, then a stroke of the piston rod 10 within the piston cylinder 11 is initiated, following a release action of the piston rod 10. The diffusion chamber 13 increases its volume gradually, such that its internal pressure decreases gradually to be even a lower pressure than the ambient atmosphere pressure, resulting in a gas suction effect which is generated by both the steam channel 2, which is in communication with the diffusion chamber 13 and is provided with no unidirectional air-tight valve, and the clean air channel 3, which is provided with the first-level unidirectional air-tight valve 32. Specifically, due to the relatively low pressure within the diffusion chamber 13, said fluid path from the feed syringe needle to the external environment is closed by the effect of the second-level unidirectional air-tight valve 42 when the stroke of the piston rod 10 begins; while an aspiration airflow is generated from the storage chamber 101 within the piston rod 10 towards the diffusion chamber 13, and such an airflow which flows out of the storage chamber may facilitate a volatilization of the standard sample stored inside the storage chamber 101 and in turn facilitate generation of the steam of the standard sample caused hereby. Similarly, the diffusion chamber 13 at a relatively low pressure opens unidirectionally said first-level unidirectional air-tight valve 32 thereto, so as to suck in an environmental gas which functions as a carrier gas for the steam of the standard sample, through the clean air channel 3.

Given that some contaminant may be easily introduced into the diffusion chamber 13 in case that ambient air is directly introduced to function as the environmental gas, then, in order to ensure that the gas sucked through the clean air channel is a clean air, in an exemplary embodiment as illustrated in FIG. 1, a gas filter device 30 for cleaning the air is additionally provided upstream of the first-level air-tight valve 32 in the clean air channel 3, and is mainly configured to filter out impurities or contaminants which are carried by the environmental gas flowing through a filter cartridge of the gas filter device 30, so as to ensure that the environmental gas flowing into the diffusion chamber may has a relatively high air cleanliness; as such, upon an detection or inspection of the sample thus fed, a mixed gas produced by the steam of the standard sample and the environmental gas may not influence adversely the detection and analysis on the standard sample as well as subsequent calibration.

By way of example, inside the filter cartridge of the gas filter device 30, there is filled with a material which has not only relatively superior gas permeability but also relatively strong filtration and adsorption properties for impurities such as water and the like; for example, the filling material may be a mixture of activated carbon and molecular sieve. The filling material may filter out and remove effectively both water and other impurities or contaminants carried in the air (i.e., the environmental gas) which enters the diffusion chamber 13 through the filter cartridge of the gas filter device 30 during the suction process of the piston assembly 1, hereby preventing effectively the steam of the standard sample which is mixed with the environmental gas inside the diffusion chamber 13 from being contaminated by impurities carried in the ambient air, and in turn preventing any adverse influence thus caused on subsequent calibration. Additionally, by way of example, as exemplarily illustrated in FIG. 1, the gas filter device 30 may further comprises a filter cartridge cover 301. In case that the filter cartridge fails or purification efficiency thereof reduces, the filling material inside the filter cartridge may be exchanged by opening the filter cartridge cover 301.

As illustrated in FIGS. 1 and 5, the piston rod 10 is driven downwards from the highest position inside the piston cylinder 11. Once the storage chamber 101 within the piston rod 10 is in communication with the steam channel 2 via the steam inlet port, the piston rod 10 displaces such that the steam outlet port communicates with the diffusion chamber 13 within the piston cylinder 11, and thus a solid sample contained within the storage chamber 101 may volatile into the steam of the sample which may be sucked through the steam channel 2 and back into the diffusion chamber 13 within the piston cylinder 11, smoothly; while the first-level air-tight valve 32 opens unidirectionally towards the diffusion chamber 13, resulting in that the filtered environmental gas which functions as the clean air may also be sucked into the diffusion chamber 13, through the first-level air-tight valve 32. Subsequently, the steam of the sample and the clean air may mix with each other within the diffusion chamber 13; and the piston rod 10 continues to be driven downwards so as to increase progressively the gas pressure inside the diffusion chamber 13, resulting in that the second-level air-tight valve 42 is opened, and the mixed gas which is formed by the steam of the standard sample and the clean air collectively and is to be detected or inspected may be exhausted from the diffusion chamber through the second-level air-tight valve 42 and the feed syringe needle 4.

In the illustrated embodiments, the preparation and feed apparatus of the standard sample for calibration of the trace-analysis instrument may be shaped to be substantially in a form of a conventional piston syringe, and the piston rod 10 is provided with the storage chamber 101 which penetrates radially therethrough so as to accommodate the sample and to generate the steam of the standard sample, and the steam of the standard sample is communicated back to the diffusion chamber 13 within the piston cylinder 11 through the external steam channel 2, and is mixed with the filtered clean air which is also communicated to the diffusion chamber 13 through the external clean air channel 3, and finally, the mixed gas for calibration is thus generated by both the steam of the standard sample and the clean air, and urged by the piston rod 10 so as to be further injected into an injection port of a GC-IMS (i.e., gas chromatograph-ion mobility spectrometer) via the feed syringe needle 4, such that the inspection analysis and calibration on the sample may be implemented. Hereby, when the trace-analysis instrument is being calibrated, specific calibration operations are implemented by loading the sample directly into the storage chamber 101 of the preparation and feed apparatus, and in turn inserting the whole preparation and feed apparatus into the injection port of the trace-analysis instrument so as to implement the inspection analysis and calibration on the sample, with neither any requirement on any individual sample preparation step additionally used to prepare a test sample for calibration, nor any requirement on organic solvent or a dedicated sample application/dispensing tool (e.g., a calibration pen), resulting in that the trace-analysis instrument is simple and convenient to carry and use, and the substance for calibration is also convenient to be stored and exchanged; moreover, the trace-analysis instrument is also safe, reliable and environmentally friendly.

A specific construction of the preparation and feed apparatus are set forth in detail hereinafter on a basis of FIG. 1 in view of other figures.

Figure 2:
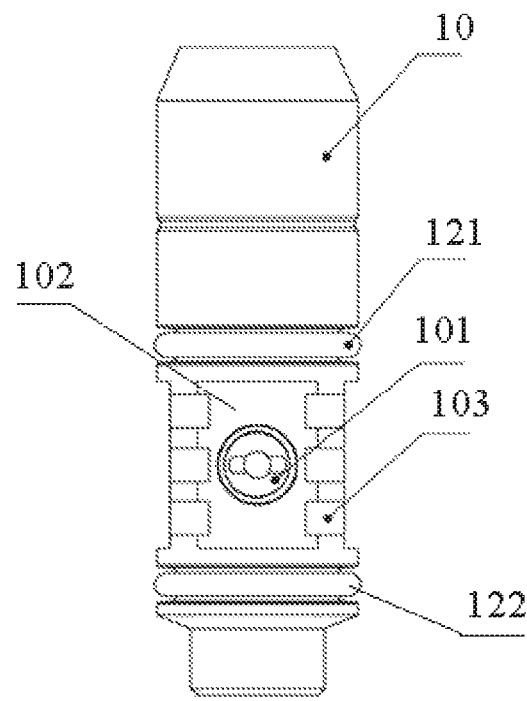
FIG. 2 illustrates a structural schematic view of a piston rod of the preparation and feed apparatus as illustrated in FIG. 1.
Figure 3:
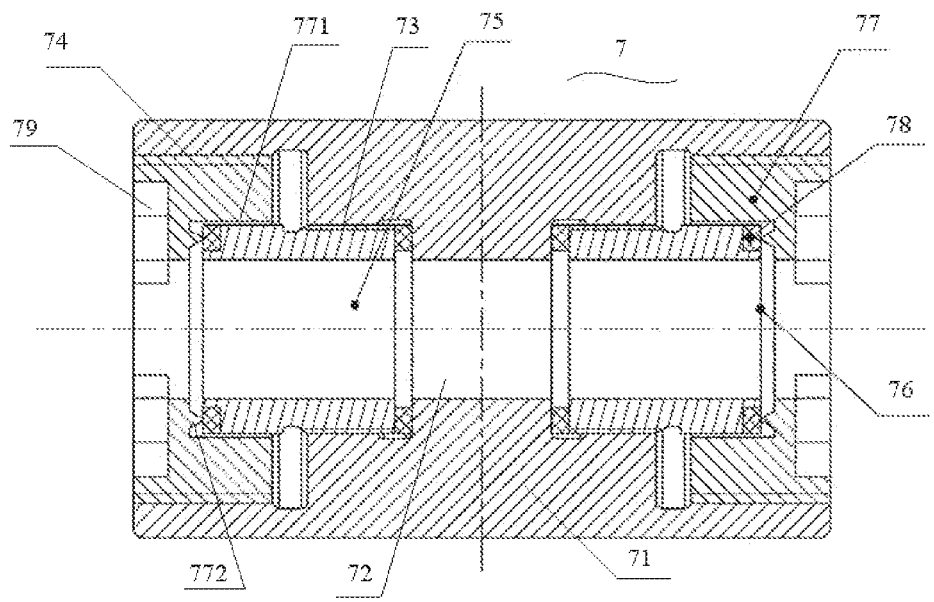
FIG. 3 illustrates a structural schematic view of a sample vessel accommodated within the piston rod as illustrated in FIG. 2.

FIG. 2 illustrates a structural schematic view of a piston rod 10 of the preparation and feed apparatus as illustrated in FIG. 1; and FIG. 3 illustrates a structural schematic view of a sample vessel accommodated in the storage chamber 101 within the piston rod 10 as illustrated in FIG. 2.

Firstly, on the basis of FIG. 1, in view of other FIGS. 2-3, various components in the preparation and feed apparatus of the standard sample which are used to store a solid sample and to generate the steam of the sample are set forth in detail.

By way of example, as illustrated in FIGS. 1 and 2, in a central portion between the upper sealing ring 121 and the lower sealing ring 122 of the piston rod 10, two opposed side end surfaces 102 are sectioned diametrically opposite to each other, e.g., preferably in a rectangular shape; and the storage chamber 101 as above extends radially so as to penetrate through the piston rod 10 and to terminate at both ends itself respectively at the two opposed side end surfaces 102. The storage chamber 101 is configured to accommodate a sample vessel 7, which sample vessel contains herein the solid standard sample or a permeation tube filled with a standard sample. Furthermore, as illustrated in FIG. 2 in more detail, for example, it may be preferable that pairs of gas guiding slots 103 are arranged to be symmetric axially relative to a longitudinal axis of the piston rod 10, at both sides of each side end surface 102 which extend longitudinally. For example, as illustrated, there are three pairs of the gas guiding slots 103, each pair being arranged to be symmetric axially. Furthermore, each of the gas guiding slots 103 is for example formed by cutting radially inwards into a slot, at a cylindrical surface of the piston rod 10 adjacent to the side end surface 102, bottom surface of each of the gas guiding slots 103 being constructed to be flush with or slightly shallower than the side end surface 102, such that once the piston rod 10 is inserted into the piston cylinder 11, a space defined between each side end surface 102 of the piston rod 10 and the inner wall of the piston cylinder 11 communicates with the external of the piston rod 10 via the gas guiding slots 103. The illustrated gas guiding slots 103 function as convergent fluid paths, so as to facilitate acceleration of the fluid passing therethrough based on the Bernoulli's Principle, such that the provision of the gas guiding slots may facilitate discharge of the steam of the sample outside the piston rod 10 by diffusion or blowing out of the storage chamber 101, e.g., to the diffusion chamber 13 through the steam channel 2.

As illustrated in FIG. 3, in the illustrative embodiment, the sample vessel 7 which is removably accommodated in the storage chamber 101 is configured to substantially match a shape of the inner space of the storage chamber 101, for example, the sample vessel 7 is in a form of cylinder shape as illustrated, or alternatively in a form of capsule shape. The sample chamber 7 is configured to contain therein the standard sample which is solid or liquid tending to be evaporated or volatilized to form sufficient steam for identification in detection, such as TNT (i.e., trinitrotoluene) powders, AN (ammonia nitrate) powders, BHT (butylated hydroxyl toluene), and nicotinamide, and the like; or alternatively configured to contain therein a permeation tube filled with the standard sample. Alternatively or additionally, the standard sample may be mounted in the sample vessel 7 by a fixation material such as a metallic wire mesh or glass fiber.

As an exemplary embodiment, as illustrated in FIG. 3, the sample vessel 7 comprises: a housing 71; a pair of stepped counter bores; at least one sample storage device, e.g., two sample storage device as illustrated; and a pair of vessel covers for each sample storage device. The housing 71 defines a cavity 72 extending therethrough, as illustrated in FIG. 3, the housing 71 is for example a substantially hollow cylinder, and is provided with both a through-hole which is centralized axially and thus functions as the cavity therethrough, and the pair of stepped counter bores which are recessed inwards axially at both ends thereof, each stepped counter bore comprising a first counter bore 73 and a second counter bore 74 which are arranged co-axially, and the first counter bore 73 having a smaller cross section dimension (e.g., diameter) and a larger depth recessed inwards axially as compared with those of the second counter bore 74. And each sample storage device is receivable, e.g., in a positive-fit manner, within each first counter bore 73 and comprises: a sample receptacle 75 which is hollow and arranged axially; and a pair of micro-pore filtration membranes 76 which abut axially from outside inwards against and thus seal both ends of the sample receptacle 75. The sample receptacle 75 is provided with a penetrating inner chamber which is shaped and dimensioned to be completely consistent with the cavity 72. The micro-pore filtration membranes 76 are configured to sieving and filtering material passing therethrough selectively so as to ensure that substantially only the steam of the sample may flow through, for example, preventing impurities or contaminants such as water molecules, ammonia molecules and the like which are carried in the steam of the sample from entering, i.e., so as to avoid any contamination caused thereby to a chromatographic column or a drift tube located at a backend, i.e., downstream. Besides, the micro-pore filtration membranes 76 may also for example restrict formation of clusters so as to enhance resolutions of backend instruments. There are also a pair of vessel covers 77 used for the pair of the sample storage devices respectively, each vessel cover being constructed to be a hollow cylinder and is also provided with a penetrating inner chamber which is shaped and dimensioned to be completely consistent with the cavity 72. And each cover 77 is also shaped and dimensioned to be adapted to be receivable within the second counter bore 74 and to encapsulate circumferentially the sample storage device in a positive fit manner once the sample storage device is received within the first counter bore 73 in a positive fit.

By way of example, as illustrated in FIG. 3, each vessel cover 77 is provided with a recess 771 at an inner end thereof, which inner end is arranged to face the sample storage device, and the recess is shaped and dimensioned at its internal cross section to be adapt to shapes and dimensions of external cross sections of both the sample receptacle 75 and the micro-pore filtration membrane 76 abutted against the sample receptacle 75. More specifically, for example, in a condition that both the sample receptacle 75 and the micro-pore filtration membrane 76 are constructed to have a round cross section respectively, the recess 771 is constructed correspondingly to be a recessed portion having a round cross section so as to accommodate at least partially a portion of the sample storage device which is exposed to the second counter bore 74 from the first counter bore 73.

In addition, in order to facilitate firmly securing the sample receptacle 75 into the housing 71 by the vessel cover 77 in an abutting manner, by way of example, the second counter bore 74 is a threaded hole, and correspondingly, the vessel cover 77 is constructed to be provided with an external screw thread for screwing into the second counter bore 74. However, in this circumstance, provided that the recess 771 abuts against the micro-pore filtration membrane 76 and the sample receptacle sequentially in a surface-contact manner, then, when the vessel cover 77 is threaded to secure the sample storage device, since a contact surface of the recess 771 with the micro-pore filtration membrane 76 may rotate clockwise or counterclockwise relative to the micro-pore filtration membrane 76, it tends to lead to a wrinkle of the micro-pore filtration membrane which is in a form of a laminated sheet, resulting in that a portion of the micro-pore filtration membrane may collapse while some other portion(s) thereof may have the micro pores thereon enlarged, or even resulting in fracture failure due to crush or tear of the micro-pore filtration membrane. Furthermore, in order to ensure completeness of the micro-pore filtration membrane and to further ensure that the produced steam of the sample is processed perfectly by the sieving of the micro-pore filtration membrane before escaping from the sample vessel 7, then, on the one hand, as illustrated in FIG. 3, the recess 771 is further provided with tooth-shaped projections 772 at an inner surface thereof facing the micro-pore filtration membrane 76, for example, a plurality of tooth-shaped projections 772 which are distributed on the inner surface uniformly, such that the surface contact turns into point contacts, minimizing a follow-up motion of the micro-pore filtration membrane 76 during the process of screwing the vessel cover 77, and thus ensuring that the micro-pore filtration membrane 76 is secured, with rarely any displacement thereof, between both an outer side of the sample receptacle 75 in the axial direction and the recess 771 of the vessel cover 77, by abutting against them. On the other hand, as in the illustrated embodiment, in order to ensure that the sample receptacle 75 is sealed and secured within the housing 71, and that the tooth-shaped projections 772 are not in direct contact with the micro-pore filtration membrane 76, and further to prevent any unfiltered gas in the sample receptacle which fails to be sieved from escaping directly to the penetrating inner chamber of the vessel cover 77, then, gasket(s) 78, e.g., in a form of O-ring silicone gasket, may be provided, between the sample receptacle 75 and a bottom surface at an innermost side of the first counter bore 73 in the axial direction, and between/or between the micro-pore filtration membrane 76 and the tooth-shaped projections 772, which may prevent crush of the filtration membrane and escape of the sample.

Continuing to refer to FIG. 3, in order to ensure the team of the sample which is sieved and filtered completely may escape from the vessel cover 77, an outboard end of the vessel cover 77 may be constructed to be aligned and flush with a plane at an end of the housing 71 into which end the vessel cover itself is embedded once the vessel cover is secured in position within the housing 71, and the outboard end of the vessel cover 77 may further be provided with flare grooves 79 enveloping an outlet of the cavity 72. And adaptively, for example, in one exemplary embodiment as illustrated in FIG. 1, the storage chamber 101 may be a radial through-hole which is formed on the piston rod 10 and provided with a flaring slot, such that the flaring slot cooperates with the flare grooves 79 of the sample vessel 7, not only facilitating diffusion of the steam of the sample into the steam channel 2, but also essentially enlarging a scope occupied by the storage chamber 101 in the longitudinal direction of the piston assembly 1 by such an arrangement. As such, the arrangement also contributes to ensure a communication between the storage chamber 101 and the steam channel 2 via an export air tap 21 at a fixed position over an even larger scope of displacement of the piston.

Turning back to refer to FIG. 1 hereinafter, in view of other drawings. e.g., FIGS. 2-4, various components in the preparation and feed apparatus of the standard sample which are configured to deliver gas are set forth in great detail as below.

According to an illustrative embodiment, by way of example, as illustrated on the left side in FIG. 1, the steam channel 2 which is located on the outside of the piston cylinder is constructed by a bent steam connection pipe 23. And in order to facilitate a circulation of the produced steam of the sample from the piston assembly 1 to the steam channel 2, e.g., both the export air tap 21 and a return air tap 22 which project outwards radially are provided additionally, on the outside of a cylinder body of the piston cylinder 11, and the steam connection pipe 23 is arranged to connect between the export air tap 21 and the return air tap 22, for guiding the steam of the sample after sieving and filtration by the micro-pore filtration membrane 76, to flow into the diffusion chamber 13 which is defined among a lower portion of the piston rod 10, the piston cylinder 11 and the lower sealing ring 122, from the sample vessel 7 accommodated within the storage chamber 101 of the piston rod 10 via the steam connection pipe 23 externally located.

Figure 4:
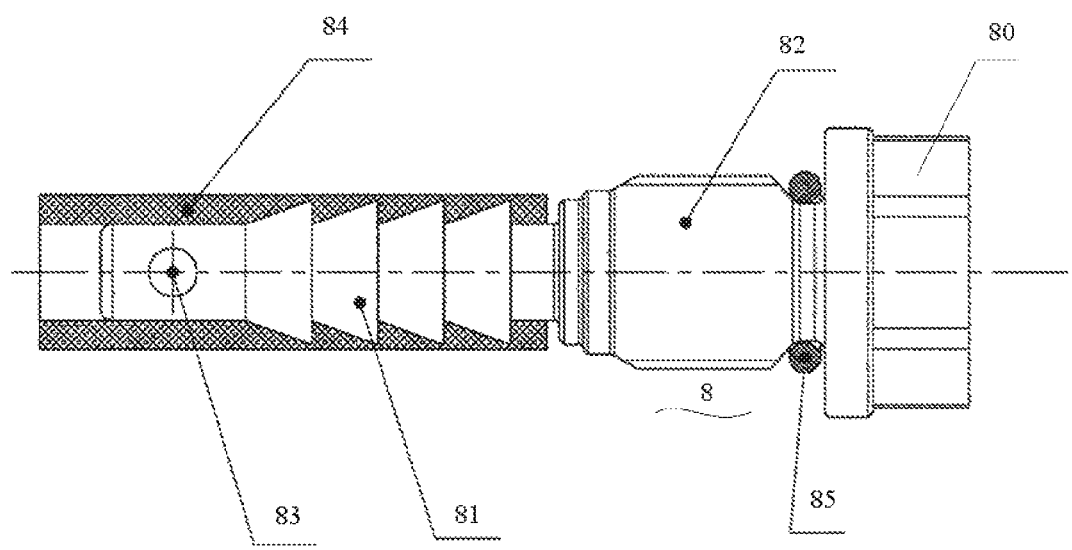
FIG. 4 illustrates a schematic view of a valve core construction which functions as a unidirectional air-tight valve, in the preparation and feed apparatus as illustrated in FIG. 1.

Then, FIG. 4 illustrates a schematic view of a valve core construction which functions as a unidirectional air-tight valve, in the preparation and feed apparatus as illustrated in FIG. 1.

By way of example, according to an exemplary embodiment as illustrated in FIGS. 1 and 4, a valve core construction functions as the first-level air-tight valve 32 and/or the second-level air-tight valve 42 opened unidirectionally. In the embodiment as illustrate in FIG. 4, for example, the valve core construction mainly comprises a hollow valve core body 8. As a specific example, the valve core body 8 for example comprises a trailing connection portion 80 at a trailing portion of the valve core body; a pagoda-shaped connection head 81 provided at a leading portion of the valve core body; and a valve core middle portion 82 provided between the trailing connection portion 80 and the pagoda-shaped connection head 81, the pagoda-shaped connection head 81 being provided with a valve core exhaust port 83, which is located laterally at a front end of the pagoda-shaped connection head 81. As an additional exemplary embodiment, as illustrated, the valve core construction further comprises an elastic sealing sleeve 84 within which the pagoda-shaped connection head 81 is encapsulated circumferentially, e.g., a rubber sealing sleeve, and the valve core exhaust port 83 is sealed by the pagoda-shaped connection head 81 and the sealing sleeve 84 encapsulating circumferentially. Upon operation of the valve core construction, it is required that a gas flow may flow from the trailing connection portion 80 into a hollow interior portion of the valve core body 8 above all, and then, with the action of a pressure difference between the trailing portion of the valve core construction and the environment where the leading portion of the valve core body 8 is located, the gas flow may prop up the sealing sleeve on an external surface of the pagoda-shaped connection head 81 at the leading portion of the valve core body 8 so as to implement a gas communication. For air-tightness, by way of example, a fluorine-rubber O-ring sealing ring 85 may further be provided on the valve core body 8.

For example, in an exemplary embodiment as illustrated in FIG. 1, the first-level air-tight valve 32 of the preparation and feed apparatus in the disclose is chosen as the above valve core construction, with its trailing connection portion being connected with an outlet of the filter cartridge of the gas filter device 30 directly or through the bent pipe indirectly; and its pagoda-shaped connection head being in communication with the diffusion chamber 13 via the valve core exhaust port thereon, so as to implement an unidirectional inflow of the clean air after filtration. Alternatively or additionally, in another exemplary embodiment as illustrated in FIG. 1, the second-level air-tight valve 42 is also chosen as the above valve core construction, with its trailing connection portion being connected with the diffusion chamber directly, and its pagoda-shaped connection head being in communication with the needle inlet port 41 of the feed syringe needle 4 via the valve core exhaust port thereon, so as to implement an unidirectional outflow of the mixed gas of both the steam of the standard sample and the filtered clean air.

Then, turning back to refer to FIG. 1, according to an exemplary embodiment as illustrated, e.g., as illustrated on the right side in FIG. 1, the clean air channel 3 which is located on the outside of the piston cylinder comprises the gas filter device 30, another bent pipe, and the valve core construction which functions as the first-level air-tight valve 32. Moreover, as illustrated in FIG. 1, in an additional exemplary embodiment, near a piston cylinder flange 111 at the bottom portion of the piston cylinder, an additional mounting boss 112 is provided, which projects outwardly in a radial direction at a side towards the clean air channel 3, and is provided with a flat upper surface and an elongate through-hole extending therethrough into the piston cylinder 11, the flat upper surface being adapted to bear the gas filter device 30 while the first-level air-tight valve 32 of the extended valve core construction being adapted to be inserted into the elongate through-hole inside the mounting boss 112.

Furthermore, continuing to refer to FIGS. 1 and 5, various components which are configured to implement gas mixing inside the diffusion chamber 13 and to discharge the mixed gas of the standard sample to be detected from the diffusion chamber are set forth in detail.

As an exemplary embodiment, as illustrated in FIGS. 1 and 5, the feed syringe needle 4 is configured to implement a puncture of a spacer at the injection port of the GC-IMS so as to implement sample introduction. Said feed syringe needle 4 is for example exchangeable, e.g., is provided with a threaded screw coupling interface for thread screw connection with the bottom portion of the piston cylinder, and is sealed by the fluorine-rubber or silicone rubber O-ring sealing ring. The needle may be chosen as a headspace sampling needle which is commercially available from CTC Corporation, Swiss or Beijing Leide Technology, Inc. Moreover, as an additional exemplary embodiment as illustrated in FIGS. 1 and 5, at the piston cylinder flange 111 at the bottom portion of the piston cylinder 11, a syringe cylinder cap boss 5 is additionally installed which is mounted in a flange-joint manner. The syringe cylinder cap boss 5, by way of example as illustrated, is constructed to have a notch. On the one hand, the notch is configured to be mounted with a syringe cylinder cap 6 for protection of the feed syringe needle 4 in a removable fit, and on the other hand, the notch is adapted to get stuck at a cap for the spacer at the injection port of the GC-IMS so as to protect the needle for facilitating sample feeding operation, following a removal of the syringe cylinder cap 6 upon detection/inspection. And the syringe cylinder cap is preferred to be an organic glass hood which prevents effectively the preparation and feed apparatus of the disclosure from bending at the needle during transportation or storage thereof, and is capable of providing a dustproof protection on the needle.

Operational steps of calibration of the GC-IMS to be calibrated by using the aforementioned preparation and feed apparatus of the standard sample for calibration of the trace-analysis instrument which is assembled to prepare and feed the mixed gas of the steam of the standard sample and the clean air, are set forth simply hereinafter, according to exemplary embodiments of the disclosure.

Firstly, a sample filling step is carried out. Above all, the piston rod 10 is removed from the piston cylinder 11 and then the sample vessel 7 is taken out of the storage chamber 101 so as to carry out filling, or replacement/refilling of the sample. Specifically, for example, the vessel cover 77 of at least one end of the sample vessel 7 is firstly unscrewed and the micro-pore filtration membrane(s) 76 may be fetched out of the housing 71 of the sample vessel 7, and the standard sample or the permeation tube filled with a standard sample may in turn be placed into the sample receptacle 75. After the filling, replacement or refilling of the sample is completed, then the micro-pore filtration membranes 76 are sequentially placed at both sides of the sample receptacle 75, and screwed up by the vessel cover 77. And there are tiny tooth-shaped projections provided at contacting locations between the vessel cover 77 of the sample vessel and the micro-pore filtration membrane 76, and there may also be O-ring silicone gasket in the sample vessel, so as to prevent crush of the filtration membranes and leakage of the sample. Next, the sample vessel 7 is reinstalled into the storage chamber 101 of the piston rod 10 and secured therein, and finally the piston rod 10 which are filled with the standard sample is also reinstalled into the piston cylinder 11, such that the filling of the sample is completed. By way of example, a fluorine-rubber O-ring sealing ring 12 is applied between the piston rod 10 and the piston cylinder 11 for air-tight sealing. Thereby the vessel cover 77 is opened/closed by screwing/unscrewing respectively, facilitating placement of the sample to be calibrated into the detachable sample vessel 7 or extraction or replacement of any residue of the sample after the detection/inspection. Alternatively or additionally, when different samples are required to carry out calibration, the switch among different samples may be implemented by direct replacement of other sample vessels 7 already filled with other different samples, so as to avoid any cross contamination and its adverse influence on subsequent calibration of back-end instrument(s) due to filling of different samples in an identical sample vessel 7.

Secondly, an operation of preparation and feed of gas is implemented. Before calibration of the instrument, for example, the piston rod 10 is driven to a sample diffusion mode as illustrated in FIG. 1 by pushing and pulling the piston handle, then the steam of the standard sample escapes from the sample receptacle(s) 75 through the micro-pore filtration membrane(s) 76 and the vessel cover(s), and in turn enters the steam channel 2 via the export air tap 21 located at left side of the piston cylinder 11 and the steam inlet port connected therewith, and finally reaches the diffusion chamber 13 via the steam outlet port, so as to mix up with the clean air which is already filtered by the gas filter device 30 located at the right side of the piston cylinder 11. The connections between the gas filter device 30 and the piston cylinder 11 and between the feed syringe needle 4 and the piston cylinder 11 are all in the form of the valve core construction which is unidirectional opened, so as to facilitate the steam of the sample entering the diffusion chamber 13 during the process of diffusion of the sample. In a condition of relatively high concentration of the steam of the sample, the steam may be diluted by a filtered clean air in proportion therebetween for performing an accurate analysis of the concentration of the sample. And when the dilution is not necessary, the gas flow may be maintained steadily and smoothly by controlling opening and closing operations of the unidirectional valve, for example the valve core construction, facilitating both adjustment of flow rate and rinsing.

When the piston rod 10 is pushed to the bottom portion of the piston cylinder 11 for sample introduction, as illustrated in FIG. 5, it is also ensured that the mixed gas of both the steam of the sample and the clean air may enter the GC-IMS instrument which requires to be calibrated successfully and effectively.

Finally, a calibration operation is performed. When a calibration of above GC-IMS is carried out by using the preparation and feed apparatus of the standard sample for calibration of the trace-analysis instrument of the disclosure, an operator should remove the syringe cylinder cap 6 from the feed syringe needle 4 above all, insert the feed syringe needle rapidly into the injection port of the GC-IMS to be calibrated, then push on the piston handle to press the mixed gas of both the steam of the standard sample stored in the diffusion chamber 13 and the filtered clean air from ambient environment into the injection port of the GC-IMS, and then drive the mixed gas subsequently by a feed carrier gas of the GC to pass through the chromatographic column and then to the IMS for detection analysis of the sample. The instrument records and stores the result of this analysis and compares it with that in a standard laboratory environment condition, so as to determine present parameters of its operation environment and then to take advantages of such parameters.

Similarly, in other embodiments, various modifications and variations may be implemented, based on above fundamental embodiment.

First Extension Embodiment

Additionally or alternatively, according to an inventive concept of the disclosure, on the basis of the preparation and feed apparatus of a standard sample for calibration of a trace-analysis instrument as in precedent embodiments, in order to facilitate generation of the steam of the standard sample, by way of example, in another exemplary embodiment of the disclosure, there is further provided a modified preparation and feed apparatus of a standard sample for calibration of a trace-analysis instrument. On the basis of the preparation and feed apparatus as illustrated in FIG. 1, an additional blowing device is provided within or adjacent to the storage chamber 101 of the piston rod 10, and is located opposite to a side of the storage chamber 101 where the storage chamber is in communication with the steam channel, and is in communication with the interior 101 of the storage chamber 101 so as to blow inwards the sample vessel 7 received therein, so as to accelerate (i.e., speed up) the volatilization of a solid sample, for example, and to blow out a steam or an aerosol of sample for calibration thus generated from the storage chamber 101 through the export air tap 21 towards the steam inlet port of the steam channel 2.

In this exemplary embodiment, the blowing device may be in various forms, e.g., a rubber bulb suction or a nozzle. Furthermore, by way of example, the blowing device, e.g., the nozzle, may be configured to spray or eject a hot air jet. When the hot air is blown towards the sample, both dispersion and volatilization of the sample may be accelerated so as to enhance the efficiency of production of the steam of the sample. Further, the additional nozzle may be arranged to be close to the stacked sample so as to obtain better effect of blowing and heating. Moreover, the additional nozzle may for example be chosen as a plurality of nozzles which are adjustable such that the blown air jet is oriented to conform to the direction of the aspiration airflow due to suction of the steam of the sample by the diffusion chamber 13 via the steam channel 2 such that the airflow ejected by the additional nozzle contributes to accelerate the suction of the sample stream. As such, the direction in which the additional nozzle(s) blow an airflow may be adjusted to be in a same or similar direction as compared with the aspiration airflow for suction of the steam of the sample, so as to ensure that the steam of the sample may be exhausted more effectively.

In addition to above contents concerning the blowing device, the preparation and feed apparatus is essentially identical to that in the fundamental embodiment, and the same or similar contents thus may not be repeated here once again, for brevity.

Second Extension Embodiment

Additionally or alternatively, according to an inventive concept of the disclosure, on the basis of the preparation and feed apparatus of a standard sample for calibration of a trace-analysis instrument as in precedent fundamental and first extension embodiments, in order to facilitate generation of the steam of the standard sample and to ensure simultaneously a sieve and purification of the steam of the standard sample, by way of example, in yet another exemplary embodiment of the disclosure, there is further provided one more modified preparation and feed apparatus of a standard sample for calibration of a trace-analysis instrument. On the basis of the preparation and feed apparatus as illustrated in FIG. 1, an additional heater is provided within or adjacent to the storage chamber 101 in the piston rod 10, e.g., upstream or downstream of the storage chamber 101. For example, the heater is a heating rod or a heating filter screen provided at a side of the storage chamber 101 in communication with the steam channel, so as to facilitate the volatilization of the sample to emit the steam or to generate an aerosol. By way of example, in a condition that a heating filter screen is provided additionally, one the one hand, sample particles may be prevented from entering the steam channel so as to block the latter; on the other hand, both heating and volatilization of solid sample particles may be facilitated.

In addition to above contents concerning the heater, the preparation and feed apparatus may be considered to be essentially identical to those in the fundamental embodiment and in the first extension embodiment, and the same or similar contents thus may not be repeated here once again, for brevity.

Similarly, in other embodiments, various modifications or variations may be implemented on the basis of above first embodiment.

In another exemplary embodiment, preferably, at least one of the upper sealing ring 121 and the lower sealing ring 122 comprises a plurality of sealing rings which are arranged inline axially.

As illustrated clearly in FIG. 1, in the illustrative embodiment, the piston rod is configured to be in a form of cylinder, e.g., a cylindrical body. And for example, the piston cylinder is a hollow one, e.g., a cylinder having a hollow cylindrical inner cavity. More specifically, the piston cylinder is arranged to be coaxially and in positive fit with the piston rod received therein such that the piston rod is movable longitudinally inside the piston cylinder 11. Correspondingly and preferably, the peripheral sealing ring is a sealing ring whose cross section is shaped to be in positive fit with that of the cylindrical piston rod 10, for example, O-ring sealing ring. However, it may be comprehensible by those skilled in the art that, the disclosure may not be limited to the illustrated embodiments; for example, the piston rod may be shaped to be in the form of a prism. And correspondingly, the interior of the piston cylinder 11 is still shaped to be in positive fit with the piston rod in terms of respective shapes, such that the piston rod is movable longitudinally within the piston cylinder 11.

By way of example, more preferably, the feed syringe needle 4 is arranged coaxially with and centralized relative to both the piston rod and the piston cylinder. As such, when the piston rod 10 moves to enlarge a volume occupied thereby within the piston cylinder 11, so as to compress the volume of the diffusion chamber 13, the gas enclosed and sealed within the diffusion chamber 13 may flow uniformly over the entire cross section of the diffusion chamber to a needle inlet port 41 of the feed syringe needle 4 which is centralized, and flow through the feed syringe needle 4, and then be accelerated and ejected out of a needle outlet port 43 based on the Bernoulli's Principle due to constriction of fluid path, facilitating calibration by taking advantage of the rapid response property of IMS.

In consideration of both the influence of the minimization of the diffusion chamber on the steam of the standard sample, and respective functions/efficacies required respectively by the fixed piston cylinder 11, the movable piston rod 10 and the sealing rings therebetween for sealing and follow-up movement in the piston assembly, the specific materials of various components of the piston assembly may be selected. By way of example, the piston rod 10 and the piston cylinder 11 may be formed preferably by stainless steel and is processed by passivation; while the sealing rings are for example formed preferably by fluorine-rubber or silicone rubber.

In another supplementary embodiment, as illustrated in FIG. 1, by way of example, in order to facilitate driving the piston rod 10 to move within the piston cylinder 11, the piston assembly 1 further comprises a piston handle 14 which comprises an upper portion 141 of the handle which is in a form of inverted truncated hemisphere processed by edge rounding and thus adapted to be grasped by human hands, and a lower portion 142 of the handle which is in a form of truncated cone and thus provided with a flat joint surface with the upper portion 141, the flat bottom surface of the lower portion 142 being adapted to abut and contact closely with a flat upper surface of the piston rod 10. Furthermore, in order to implement a secured bond between the piston handle 14 and the piston rod 10, the lower portion 142 is further provided with a screw joint 1421 which projects downwards from the flat bottom surface thereof, for example, the screw joint 1421 being formed integrally with the piston handle 14, or being firmly secured to the piston handle via a threaded connection, a bayonet connection, or a mortise and tenon joint fit, etc. The screw joint 1421 may be threaded into a threaded hole formed into the upper portion of the piston rod 10, or directly threaded into the upper portion of the piston rod, by an external thread on the screw joint 1421. Once the standard sample diffuses into the diffusion chamber, the piston rod 10 tends to be driven to reach the bottom portion of the piston cylinder 11, e.g., by pressing on the piston handle manually, so as to argue the mixed gas of the seam of the standard sample and the filtered clean air within the diffusion chamber 13 from the second-level air-tight valve 42 into the injection port of the GC-IMS via the feed syringe needle 4 for calibration and sample analysis.

Beneficial technical effects of the embodiments of the disclosure are listed as below.

Firstly, the preparation and feed apparatus of a standard sample for calibration of a trace-analysis instrument as provided in the embodiments of the disclosure, is especially suitable for calibration of GC-IMS, and other trace analysis instrument such as GC, or GC-MS. The preparation and feed apparatus for calibration not only simplify the calibration but also is convenient to carry and use and thus facilitate both storage and replacement or exchange of the material to be used for calibration, and thus is also safe, reliable and environmentally friendly.

Secondly, since above GC-IMS in the second aspect comprises the preparation and feed apparatus as in the first aspect, then it also has similar beneficial technical effects to those of the preparation and feed apparatus, without repeating herein any more.

Various embodiments of the present application have been illustrated progressively, the same or similar parts of which can be referred to each other. The differences between each embodiment and the others are described in emphasis.

It should be appreciated for those skilled in this art that the above embodiments are intended to be illustrated, and not restrictive. For example, many modifications may be made to the above embodiments by those skilled in this art, and various features described in different embodiments may be freely combined with each other without conflicting in configuration or principle.

Although the disclosure is described in view of the attached drawings, the embodiments disclosed in the drawings are only intended to illustrate the preferable embodiment of the present disclosure exemplarily, and should not be deemed as a restriction thereof.

Although several exemplary embodiments of the general concept of the present disclosure, i.e., a preparation and feed apparatus of standard sample for calibration of trace-analysis instrument and its components, have been shown and described, it would be appreciated by those skilled in the art that various changes or modifications may be made in these embodiments without departing from the principles and spirit of the disclosure and lie within the scope of present application, which scope is defined in the claims and their equivalents.

As used herein, an element recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

LIST OF REFERENCE NUMERALS

1 piston assembly
10 piston rod
101 storage chamber
102 side end surface
103 gas guiding slot 11 piston cylinder
111 piston cylinder flange
112 mounting boss
12 peripheral sealing ring
121 upper sealing ring
122 lower sealing ring
13 diffusion chamber
14 piston handle
141 upper portion of the handle
142 lower portion of the handle
1421 screw joint
2 steam channel
21 export air tap
22 return air tap
23 steam connection pipe
3 clean air channel
30 gas filter device
301 filter cartridge cover
31 clean air connection pipe
32 first-level air-tight valve
4 feed syringe needle
41 needle inlet port
42 second-level air-tight valve
43 needle outlet port
5 syringe cylinder cap boss
6 syringe cylinder cap
7 sample vessel
71 sample vessel housing
72 cavity
73 first counter bore
74 second counter bore
75 sample receptacle
76 micro-pore filtration membrane
77 vessel cover
771 recess
772 tooth-shaped projections
78 gasket
79 flare groove
8 valve core body
80 trailing connection portion
81 pagoda-shaped connection head
82 valve core middle portion
83 valve core exhaust port
84 sealing sleeve
85 sealing sleeve

What is claimed is:

1. A preparation and feed apparatus of a standard sample for calibration of a trace-analysis instrument, wherein the preparation and feed apparatus comprises: a piston assembly, comprising: a piston cylinder; a piston rod which is received within the piston cylinder and the piston rod is provided with a storage chamber penetrating radially therethrough; and a diffusion chamber defined inside the piston cylinder and between an inner wall of the piston cylinder and the piston rod, and a steam channel which is arranged outside the piston assembly and is provided with a steam inlet port and a steam outlet port both being in communication with the piston cylinder, and wherein the piston rod is configured to be displaceable longitudinally within the piston cylinder, such that the storage chamber is communicable with the steam channel via the steam inlet port, and a condition of communication from the steam outlet port to the diffusion chamber within the piston cylinder is changeable continuously between a completely unobstructed condition and a completely occluded condition via the piston rod.

2. The preparation and feed apparatus according to claim 1, wherein the piston assembly further comprises peripheral sealing rings mounted onto the piston rod, and wherein the peripheral sealing rings are configured to abut in an airtight manner against both the inner wall of the piston cylinder and the piston rod so as to be disposed therebetween, and also configured to be displaceable longitudinally inside the piston cylinder with a displacement of the piston rod.

3. The preparation and feed apparatus according to claim 2, wherein the peripheral sealing rings comprises an upper sealing ring and a lower sealing ring which are respectively configured to be disposed at both upper and lower sides of the storage chamber, longitudinally within the piston cylinder.

4. The preparation and feed apparatus according to claim 3, wherein the diffusion chamber is delimited between the inner wall of the piston cylinder and the piston rod by the lower sealing ring, and is provided with a volume which is continuously variable with the displacement of the piston rod.

5. The preparation and feed apparatus according to claim 1, further comprising a air channel which is provided outside the piston assembly and in communication with the piston cylinder and an external environment, and is provided with a first-level air-tight valve which is opened unidirectionally towards the piston cylinder.

6. The preparation and feed apparatus according to claim 5, wherein the air channel comprises a gas filter device provided upstream of the first-level airtight valve.

7. The preparation and feed apparatus according to claim 6, wherein the gas filter device comprises a filter cartridge which is filled with activated carbon and a molecular sieve.

8. The preparation and feed apparatus according to claim 5, wherein the first-level airtight valve which is opened unidirectionally is constructed to be of a valve core construction, comprising: a hollow valve core body, comprising: a trailing connection portion at a trailing portion of the valve core body; a pagoda-shaped connection head provided at a leading portion of the valve core body; and a valve core middle portion provided between the trailing connection portion and the pagoda-shaped connection head, and an elastic sealing sleeve within which the pagoda-shaped connection head is encapsulated circumferentially, and wherein the pagoda-shaped connection head is provided with a valve core exhaust port, which is located laterally at a front end of the pagoda-shaped connection head.

9. The preparation and feed apparatus according to claim 1, further comprising a hollow feed syringe needle which is removably mounted at a bottom portion of the piston cylinder and comprises:
    a needle inlet end which is in fluid communication with the bottom portion of the piston cylinder; and
    a needle outlet end which extends outwards from the piston cylinder.

10. The preparation and feed apparatus according to claim 9, wherein the feed syringe needle is threadedly connected with the bottom portion of the piston cylinder.

11. The preparation and feed apparatus according to claim 9, wherein the feed syringe needle is in communication with the bottom portion of the piston cylinder via a second-level airtight valve which is opened unidirectionally from the piston cylinder towards the needle inlet end of the feed syringe needle.

12. The preparation and feed apparatus according to claim 11, wherein the second-level airtight valve which is opened unidirectionally is constructed to be of a valve core construction, comprising: a hollow valve core body, comprising:

a trailing connection portion at a trailing portion of the valve core body; a pagoda-shaped connection head provided at a leading portion of the valve core body; and a valve core middle portion provided between the trailing connection portion and the pagoda-shaped connection head, and an elastic sealing sleeve within which the pagoda-shaped connection head is encapsulated circumferentially, and wherein the pagoda-shaped connection head is provided with a valve core exhaust port, which is located laterally at a front end of the pagoda-shaped connection head.

13. The preparation and feed apparatus according to claim 1, wherein the storage chamber is configured to accommodate a sample vessel which is removably mounted herein.

14. The preparation and feed apparatus according to claim 13, wherein the sample vessel comprises:
- a hollow housing, which comprises a through-hole in an axial direction thereof and a pair of stepped counter bores recessed axially at both ends thereof, each stepped counter bore comprising a first counter bore and a second counter bore which are arranged co-axially, and the first counter bore having a smaller cross section dimension and a larger depth recessed inwards axially as compared with those of the second counter bore;
- at least one sample storage device, each of which is provided within the first counter bore and comprises:
  - a sample receptacle which is hollow and arranged axially, and
  - a pair of micro-pore filtration membranes which abut axially against both ends of the sample receptacle, and
- a vessel cover, configured to press one of the pair of micro-pore filtration membrane which is located outside axially, against the sample receptacle.

15. The preparation and feed apparatus according to claim 14, wherein the vessel cover is provided with a recess at an inner end thereof, the inner end is arranged to face the sample storage device, the recess being further provided with tooth-shaped projections at an inner surface thereof facing the micro-pore filtration membrane.

16. The preparation and feed apparatus according to claim 1, further comprising a blowing device provided within or adjacent to the storage chamber in the piston rod.

17. The preparation and feed apparatus according to claim 16, wherein the blowing device is located opposite to a side of the storage chamber at which side the storage chamber is in communication with the steam channel, and is in communication with the storage chamber so as to blow inwards a sample vessel which is removably mounted in the storage chamber.

18. The preparation and feed apparatus according to claim 1, further comprising a heater provided within or adjacent to the storage chamber in the piston rod.

19. A gas chromatograph-ion mobility spectrometer, comprising the preparation and feed apparatus according claim 1.

* * * * *